US00PP27717P3

(12) United States Plant Patent
Lintott et al.

(10) Patent No.: US PP27,717 P3
(45) Date of Patent: Feb. 28, 2017

(54) ***LEUCANTHEMUM* PLANT NAMED 'REAL SUNBEAM'**

(50) Latin Name: *Leucanthemum×superbum*
Varietal Denomination: Real Sunbeam

(71) Applicants: Jennifer Muriel Lintott, Bognor Regis (GB); Charles Richard Read, Bognor Regis (GB)

(72) Inventors: Keith George Lintott, Bognor Regis (GB); Charles Richard Read, Bognor Regis (GB)

( * ) Notice: Subject to any disclaimer, the term of this patent is extended or adjusted under 35 U.S.C. 154(b) by 0 days.

(21) Appl. No.: 14/757,356

(22) Filed: Dec. 21, 2015

(65) Prior Publication Data

US 2016/0205851 P1 Jul. 14, 2016

(30) Foreign Application Priority Data

Jan. 13, 2015 (QZ) ..... PBR 2015/0086

(51) Int. Cl.
*A01H 5/02* (2006.01)

(52) U.S. Cl.
USPC ..... Plt./285

(58) Field of Classification Search
USPC ..... Plt./285
See application file for complete search history.

*Primary Examiner* — Annette Para
(74) *Attorney, Agent, or Firm* — Bethany Reid Roahrig; James M. Weatherly; Cochran Freund & Young, LLC

(57) ABSTRACT

A new cultivar of *Leucanthemum* plant named 'Real Sunbeam' that is distinguishable by tight clumping basal branching and upright plant habit, non-fading yellow flowers held on very strong flower stems and whose ray florets are arranged in two to three rows, and a large disc comprised of dense arrangement of deep golden disc florets is disclosed.

2 Drawing Sheets

Genus and species: *Leucanthemum×superbum.*
Variety denomination: 'Real Sunbeam'.

CROSS REFERENCE TO RELATED APPLICATIONS

This application claims the benefit of priority under 35 U.S.C. 119(f) to the application for European Community Plant Variety Rights which was filed for the instant plant variety on Jan. 13, 2015, File Number 2015/0086.

BACKGROUND OF THE NEW PLANT

The present invention relates to a new and distinct cultivar of *Leucanthemum* commonly known as Shasta daisy, which is grown as an ornamental plant for use in the garden and landscape. The new cultivar is known botanically as *Leucanthemum×superbum* and will be referred to hereinafter by the cultivar name 'Real Sunbeam'.

*Leucanthemum* is a genus within the family Asteraceae in which the commonly referred to "flower" is botanically the inflorescence which is comprised of outer showy ray florets surrounding smaller disc florets.

'Real Sunbeam' arose and was selected from an ongoing breeding program which is conducted by the inventors at the inventors' nursery in West Sussex, United Kingdom. The breeding program commenced in 2006 with the aim of developing new and improved commercial varieties of *Leucanthemum*. 'Real Sunbeam' is a seedling selection that resulted from the controlled pollination in 2011 of a single plant of the inventors' proprietary *Leucanthemum* seedling code 'L1025-6' (unreleased and unpatented) as the female parent, using pollen from a single plant of the inventors' proprietary *Leucanthemum* seedling code 'L1045-5' (unreleased and unpatented) as the male parent. The inventors selected 'Real Sunbeam' in 2012 based on the criteria of tight clumping basal branching and upright habit, non-fading yellow inflorescences held on very strong flower stems, ray florets typically arranged in two to three rows, and a large disc comprised of dense arrangement of deep golden disc florets.

'Real Sunbeam' was first asexually propagated by the inventors in West Sussex, United Kingdom in 2012 using the method of vegetative division and subsequently by basal shoot cuttings. Since that time under careful observation 'Real Sunbeam' has been determined uniform, stable and true to type in subsequent generations of asexual propagation.

SUMMARY

The following traits have been repeatedly observed and represent the distinguishing characteristics of 'Real Sunbeam'. In combination these traits set 'Real Sunbeam' apart from all other existing varieties of *Leucanthemum* known to the inventor. 'Real Sunbeam' has not been tested under all possible conditions and phenotypic differences may be observed with variations in environmental, climatic, and cultural conditions, however, without any variance in genotype.

1. 'Real Sunbeam' exhibits tight clumping basal-branching and upright plant habit.
2. The foliage of 'Real Sunbeam' is dark green in color.
3. A fully expanded inflorescence of 'Real Sunbeam' is 7 cm in diameter and is comprised of ray florets arranged around a central disc.
4. The ray florets of 'Real Sunbeam' are and remain yellow in color.

5. The ray florets of 'Real Sunbeam' are arranged in two to three rows.
6. The disc florets of 'Real Sunbeam' are densely packed and deep gold in color.
7. The inflorescences of 'Real Sunbeam' are carried on a very strong stiff stems.
8. Flowering of 'Real Sunbeam' commences in June and continues until October.
9. After one year of growth in a 2 gallon container, or planted in the ground, a plant of 'Real Sunbeam' is 50 cm in height and 40 cm in width.
10. 'Real Sunbeam' is hardy in USDA Zone 5 (−20° F. or −28° C.).

BRIEF DESCRIPTION OF THE PHOTOGRAPHS

The accompanying color photographs were taken in July 2013 at the inventors' nursery in West Sussex, United Kingdom. The photographs illustrate the overall appearance of 'Real Sunbeam' showing the color of foliage and inflorescence as true as is reasonably possible to obtain in color reproductions of this type. The illustrated plants have been grown in 3 liter container outdoors, without any pruning or use of chemical growth regulators. The colors in the photographs may differ from color values cited in the detailed botanical description, which accurately describe the actual color of 'Real Sunbeam'.

BOTANICAL DESCRIPTION OF THE PLANT

Figure 1:
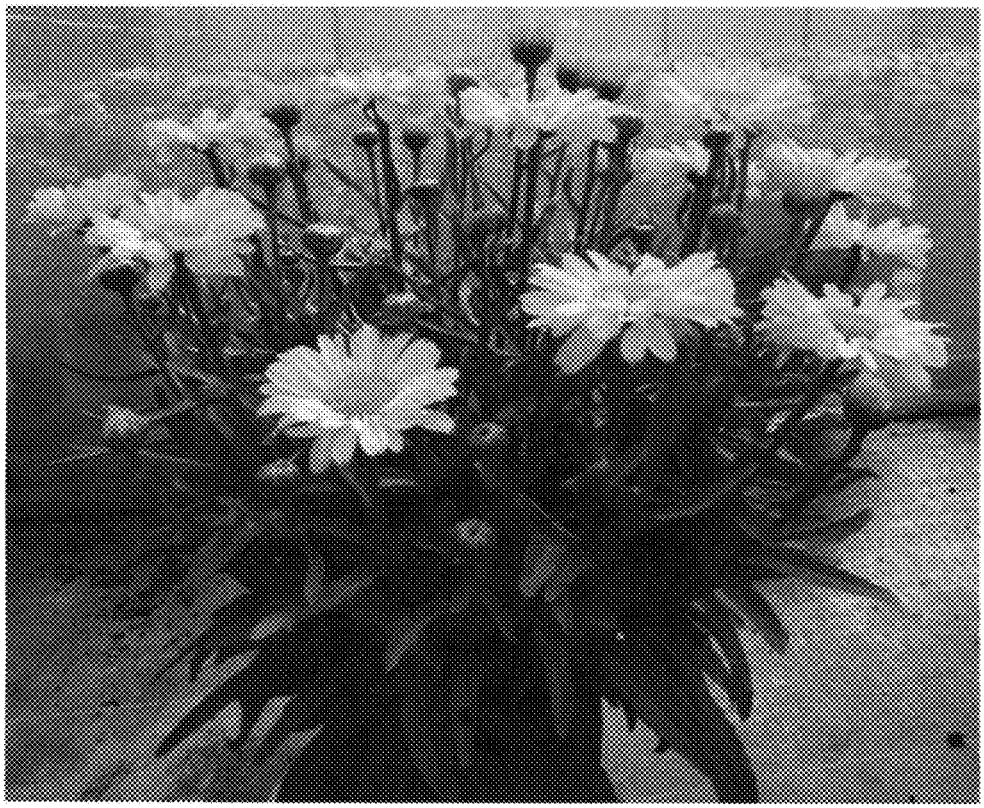
FIG. 1 illustrates an 18-month-old plant of 'Real Sunbeam' (from initial cuttings) which is growing outdoors in a 3 liter container.
Figure 2:
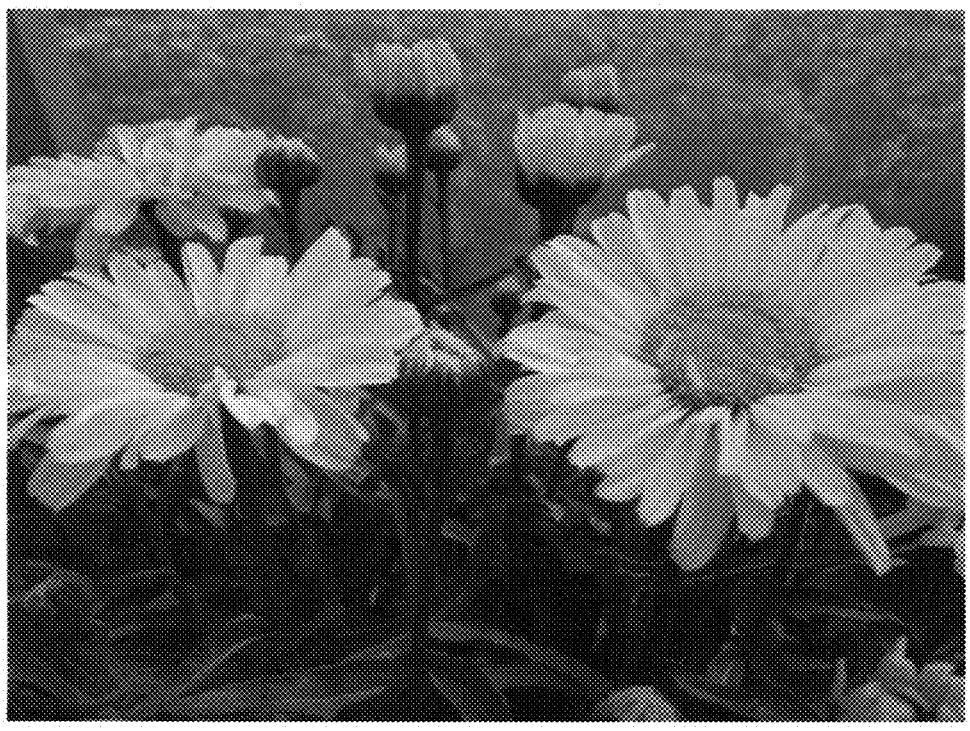
FIG. 2 depicts a close-up view of the inflorescences of 'Real Sunbeam'.

The following is a detailed botanical description of the new cultivar 'Real Sunbeam'. Observations, measurements, values and comparisons were collected in Santa Barbara, Calif. during September 2015, from a 12-month-old plant growing outdoors in the garden border. Color determinations are made in accordance with The 2007 Royal Horticultural Society Colour Chart from London, England, except where general color terms of ordinary dictionary significance are used.

Botanical classification:

*Family*.—Asteraceae (formerly Compositae).
*Genus*.—*Leucanthemum*.
*Species*.—×*superbum*.
*Denomination*.—'Real Sunbeam'.
*Common name*.—Shasta daisy.
*Habit*.—Vigorous basal-branching upright growth habit.
*Commercial category*.—Perennial.
*Use*.—For garden and landscape.
*Suggested commercial container size*.—4-inch, 1 gallon, 2 gallon containers.
*Parentage*.—*Leucanthemum*×*superbum* 'Real Sunbeam' is a seedling selection resulting from the controlled cross-pollination of the following parents: Male parent: Inventors' proprietary *Leucanthemum* seedling code 'L1045-5'. Female parent: Inventors' proprietary *Leucanthemum* seedling code 'L1025-6'.
*Propagation method*.—Basal shoot cuttings and division.
*Rooting system*.—Fine and fibrous.
*Vigor*.—Vigorous.
*Time to develop roots* (*range*).—14 to 20 days are needed for an initial cutting to develop roots.
*Temperature to develop roots* (*range*).—The recommended air temperature is 20° C. to 21° C.
*Crop time* (*range*).—7 to 8 months to produce a flowering plant in a 1 gallon container starting from a rooted cutting.
*Plant dimensions* (*one year*).—50 cm in height and 40 cm in width.
*Cultural requirements*.—Grow in full sun and rich, moist moderately fertile well-draining soil.
*Hardiness*.—USDA Zone 5.

Stem:

*Branching*.—Basal.
*Color*.—145A.
*Dimensions*.—Length, 15.0 cm; diameter (close to soil surface), 1.0 cm.
*Shape*.—Cylindrical.
*Surface*.—Smooth, glabrous.

Foliage:

*Type* (*division*).—Simple.
*Arrangement*.—Opposite.
*Internode length* (*range*).—2.5 cm to 3.0 cm.
*Margin*.—Irregularly dentate; teeth spaced at approximately 5 mm intervals, depth 1.5 mm.
*Apex*.—Acute.
*Base*.—Attenuate.
*Leaf attachment*.—Sessile.
*Leaf color* (*both surfaces*).—137D.
*Leaf shape*.—Lanceolate.
*Leaf dimensions* (*lower, oldest, leaves*).—12.0 cm in length, 1.5 to 2.2 cm in width.
*Leaf dimensions* (*upper, newest, leaves*).—5.0 cm in length, 0.8 cm in width.
*Leaf venation*.—Pinnate.
*Vein color* (*both surfaces*).—146C.
*Leaf surface* (*both surfaces*).—Glabrous.

Inflorescence:

*Inflorescence type*.—Capitulum, consisting of ray florets and disc florets.
*Inflorescence quantity* (*average*).—30 (including colored buds).
*Inflorescence diameter* (*fully opened*).—7 cm.
*Inflorescence depth*.—4.5 cm.
*Inflorescence aspect*.—Radiate. Ray florets horizontal to slightly recurved.
*Inflorescence color*.—Ray floret color: 8B when first fully open, 8C immediately prior to senescence. Central disc color: Darker than 17A, more golden than 22A.
*Fragrance*.—Musty, characteristic of wild oxeye daisy.
*Blooming season*.—June to October.
*Lastingness of inflorescence* (*range*).—10 to 14 days on the plant; ray florets are persistent.

Bud:

*Bud dimensions*.—0.75 cm in height and 1.25 cm in diameter.
*Bud shape*.—Flattened sphere.
*Bud color*.—147B.
*Bud surface*.—Glabrous.

Peduncle:

*Peduncle shape*.—Cylindrical.
*Peduncle length*.—16.0 cm to 35.0 cm.
*Peduncle diameter*.—4.0 mm to 6.0 mm.

*Peduncle surface*.—Furrowed with sparse fine hairs, color 196C.
*Peduncle strength*.—Very strong and stiff.
*Peduncle color*.—144A.

Ray florets:
*Ray floret arrangement*.—Whorled, consisting of 2 to 3 whorls of broad strap-like yellow ray florets.
*Shape*.—Quilled; corolla tube subtends single ligule or petal.
*Quantity*.—35 to 45 per inflorescence.
*Aspect*.—Initially upright as bud opens, becoming horizontal, ageing to slight reflex, no greater than 30 degrees below the horizontal.
*Corolla tube dimensions*.—3 mm in length, 1 mm in diameter.
*Corolla tube color*.—144C.

Ray floret petals:
*Shape*.—Strap-like, longitudinally furrowed forming three petal lobes.
*Surface* (*abaxial*).—Glabrous.
*Surface* (*adaxial*).—Pubescent.
*Apex*.—Emarginate (3-lobed).
*Margin*.—Entire.
*Dimensions* (*when ray floret is horizontal*).—2.0 cm to 2.5 cm in length and 5 mm to 9 mm in width.
*Color* (*both surfaces*).—8A as ray floret opens becoming 8B when ray floret is first fully open and 8C immediately prior to senescence.

Involucral bracts:
*Quantity* (*average*).—40 per inflorescence, overlapping.
*Bract color* (*abaxial and adaxial surfaces*).—147B.
*Bract length*.—9 mm to 11 mm.
*Bract width*.—3.0 mm.
*Bract apex*.—Rounded.
*Bract base* (*range*).—Rounded to truncate.
*Bract surface* (*both surfaces*).—Glabrous.
*Bract shape*.—Lanceolate.
*Bract margin*.—Ciliate, fine hairs, color 175A.

Disc floret:
*Disc diameter*.—2.6 cm to 3.0 cm.
*Disc floret quantity* (*average*).—Approximately 400 per inflorescence, massed at center of receptacle.
*Disc floret color*.—Darker than 17A, more golden than 22A.
*Disc floret dimensions*.—9 mm in length, 1 mm in diameter.
*Disc floret shape*.—Tubular.
*Disc floret petal quantity*.—Ranges from 3 to 5 in number, basally fused.
*Disc floret petal dimensions*.—3.5 mm in length, 0.75 mm to 1.0 mm in width.
*Disc floret petal color*.—Darker than 17A, more golden than 22A.
*Disc floret petal apex*.—Acute.
*Disc floret petal base*.—Truncate.
*Disc floret corolla tube*.—3.5 mm in length, 0.75 mm in diameter, color 145B.

Reproductive organs:
*Ray flowers*.—Androecium (stamens, anthers, filaments, pollen): Absent. Pistil: One, 5 mm in length. Stigma: 1 mm in length, appears bifid, color light brown. Ovary: Superior, globose, less than 1 mm in diameter, color 144D.
*Disc flowers*.—General: Stigma, style, and ovary not observed. Stamens: 5 probably fused appearing as one, length 1 mm, color 175A. Pollen: Low amount; Color yellow-orange, close to 15A. Pistil: One, less than 1 mm in length, stigma, style, ovary not observed.

Seed: None observed to date.

Pest or disease resistance and susceptibility: No specific disease or pest resistance or susceptibility has been observed or is known to the inventor.

COMPARISON WITH PARENTAL LINES AND KNOWN VARIETY

Both of the parents of 'Real Sunbeam' bear cream-yellow flowers which fade to off-white with age, whereas the flowers (ray florets) of 'Real Sunbeam' are color fast and remain yellow in color. In addition, the ray florets of both of parents are arranged in a single row, whereas the ray florets of 'Real Sunbeam' are arranged in two to three rows.

The variety of *Leucanthemum* which the inventors consider to most closely resemble 'Real Sunbeam' is *Leucanthemum* Plant Named 'Leumayel' (U.S. Plant Pat. No. 19,242). The inventors have observed that 'Leumayel' is a vigorous variety with large cream-yellow single flowers at least 10 cm in diameter, whereas 'Real Sunbeam' is compact and tightly clumping and bears smaller flowers which are 7 cm in diameter. In addition, the flowers of 'Leumayel' are pale cream in color when mature, whereas the mature flowers of 'Real Sunbeam' remain yellow in color.

We claim:

1. A new and distinct cultivar of *Leucanthemum* plant named 'Real Sunbeam' as described and illustrated herein.

* * * * *